US012691284B2

(12) United States Patent
Lucas et al.

(10) Patent No.: US 12,691,284 B2
(45) Date of Patent: Jul. 28, 2026

(54) IMPLANTABLE SENSORY SYSTEM

(71) Applicant: The Trustees of the University of Pennsylvania, Philadelphia, PA (US)

(72) Inventors: Timothy H. Lucas, Columbus, OH (US); Andrew G. Richardson, Wynnewood, PA (US); Firooz Aflatouni, Penn Valley, PA (US); Mark G. Allen, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 279 days.

(21) Appl. No.: 18/278,218

(22) PCT Filed: Feb. 22, 2022

(86) PCT No.: PCT/US2022/017258
§ 371 (c)(1),
(2) Date: Aug. 22, 2023

(87) PCT Pub. No.: WO2022/178400
PCT Pub. Date: Aug. 25, 2022

(65) Prior Publication Data
US 2024/0139514 A1 May 2, 2024

Related U.S. Application Data

(60) Provisional application No. 63/217,939, filed on Jul. 2, 2021, provisional application No. 63/152,074, filed on Feb. 22, 2021.

(51) Int. Cl.
*A61N 1/36* (2006.01)
*A61N 1/02* (2006.01)
*A61N 1/05* (2006.01)

(52) U.S. Cl.
CPC ......... *A61N 1/36135* (2013.01); *A61N 1/025* (2013.01); *A61N 1/0504* (2013.01); *A61N 1/36003* (2013.01)

(58) Field of Classification Search
CPC .. A61N 1/36135; A61N 1/025; A61N 1/0504; A61N 1/36003; A61N 1/36071
See application file for complete search history.

(56) References Cited

U.S. PATENT DOCUMENTS

| | | | |
|---|---|---|---|
| 6,993,849 B1 | 2/2006 | Campbell et al. | |
| 2003/0144710 A1 * | 7/2003 | Haugland | A61F 2/72 607/48 |

(Continued)

FOREIGN PATENT DOCUMENTS

| | | | | |
|---|---|---|---|---|
| CN | 108463163 B | * | 1/2022 | H02J 50/20 |
| WO | WO-2017120484 A1 | * | 7/2017 | A61N 1/36003 |

OTHER PUBLICATIONS

International Search Report and Written Opinion issued for corresponding PCT International Application No. PCT/US2022/017258 on Jun. 6, 2022.

(Continued)

*Primary Examiner* — Carl H Layno
*Assistant Examiner* — Maria Catherine Anthony
(74) *Attorney, Agent, or Firm* — Howson & Howson LLP

(57) ABSTRACT

A sensory system for improving and/or restoring sensation to a foot or hand of a patient. The system includes at least one force sensor implanted subcutaneously within a finger or palm of a hand or on a plantar surface of a foot of a patient and a base unit that is worn externally by the patient or is implanted subcutaneously in the patient. The force sensor is configured to transmit wireless communication signals to the base unit in response to and concerning forces sensed by the force sensor, and base unit is configured to apply peripheral nerve stimulation based on the wireless communication (Continued)

signals received from the force sensor or to transmit the sensory data to a separate neural implant. The force sensor transmits the wireless communication signals to the base unit by magnetic human body communication (mHBC).

14 Claims, 12 Drawing Sheets

(56) References Cited

U.S. PATENT DOCUMENTS

| | | | |
|---|---|---|---|
| 2009/0282930 | A1 | 11/2009 | Cheng et al. |
| 2010/0041959 | A1 | 2/2010 | Iwata et al. |
| 2011/0066046 | A1 | 3/2011 | Young et al. |
| 2014/0005743 | A1* | 1/2014 | Giuffrida ........... A61N 1/37247 |
| | | | 607/45 |
| 2018/0241483 | A1 | 8/2018 | Park et al. |
| 2018/0264263 | A1 | 9/2018 | Rosenbluth et al. |
| 2019/0158151 | A1 | 5/2019 | Shirvani et al. |

OTHER PUBLICATIONS

Hao et al., "A Hybrid-Integrated Artificial Mechanoreceptor in 180nm CMOS", 2020 IEEE Radio Frequency Integrated Circuits Symposium, RMo3A, pp. 155-158, Aug. 4, 2020.

* cited by examiner

FIG. 5
FIG. 6
FIG. 7
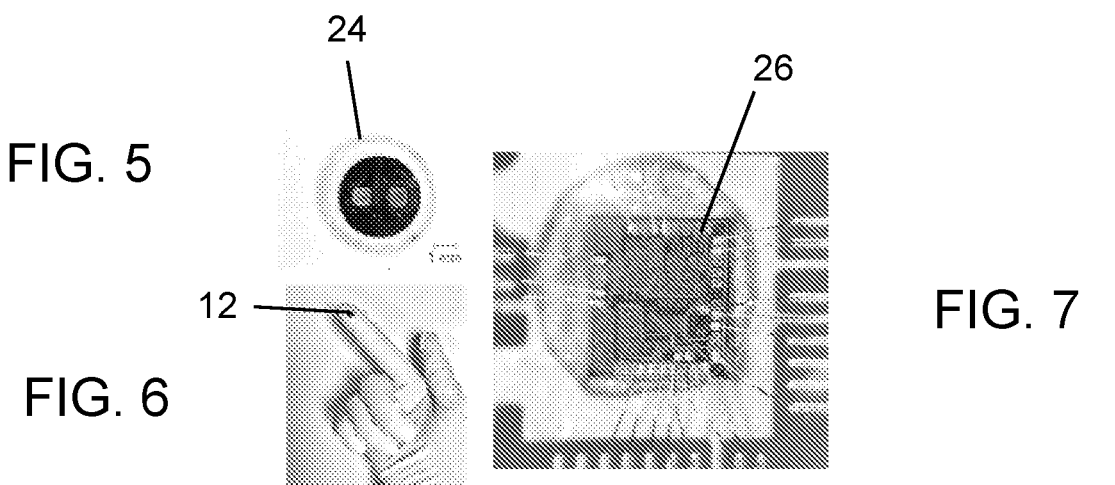
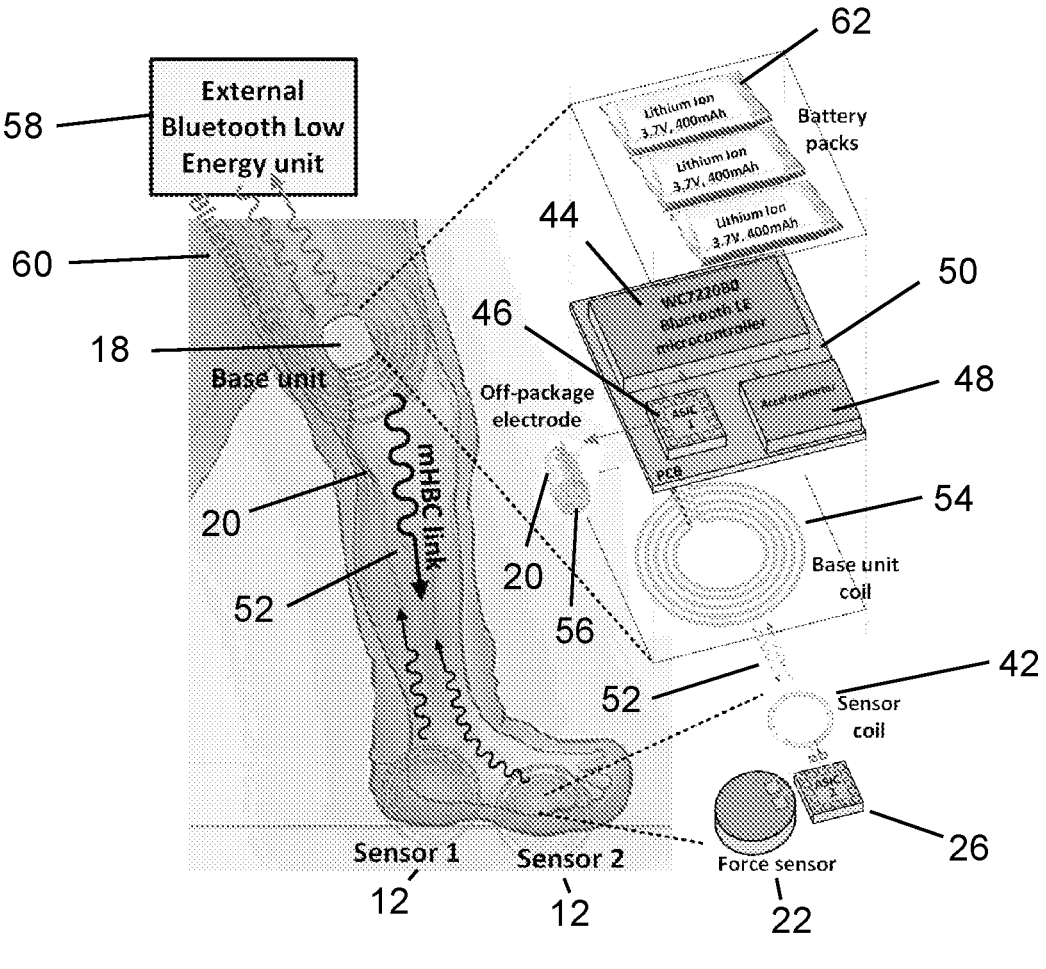
FIG. 8

(a) Generated @ the coil driver in Tx (b) Received from the sensor

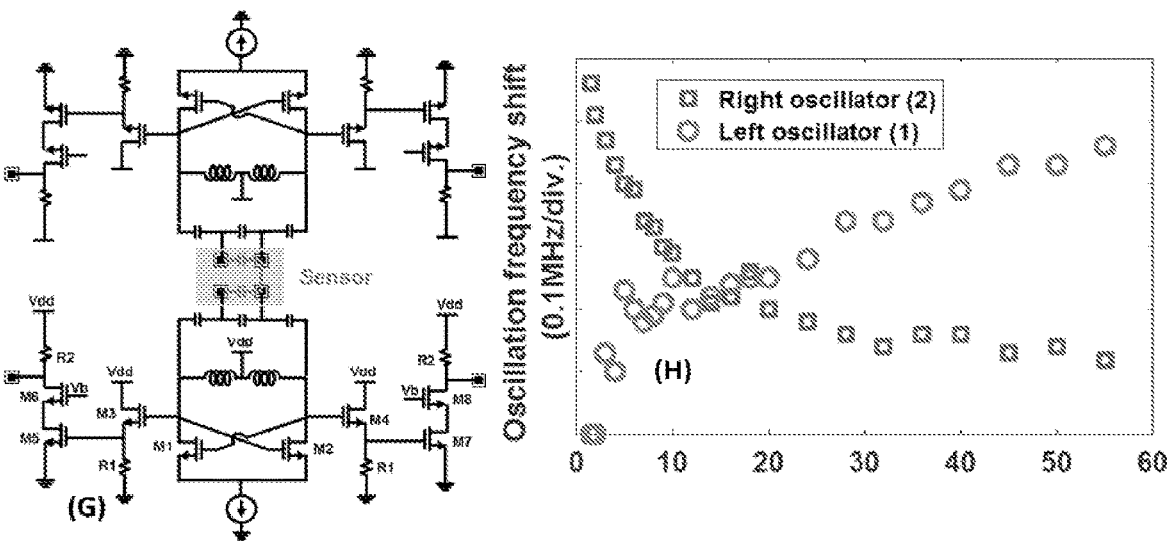
FIG. 20G
FIG. 20H
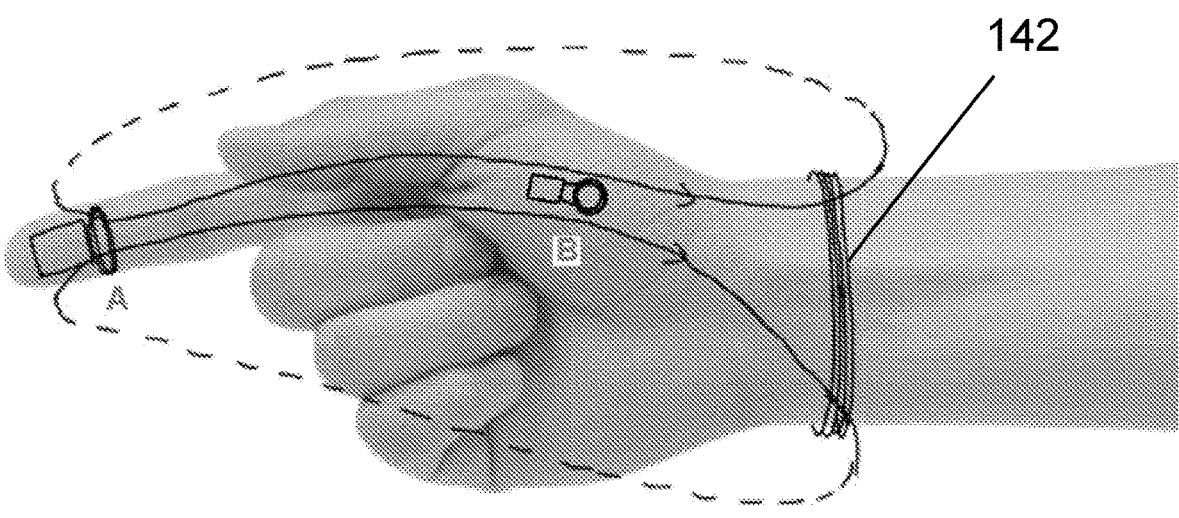
FIG. 21

IMPLANTABLE SENSORY SYSTEM

STATEMENT REGARDING FEDERALLY SPONSORED RESEARCH OR DEVELOPMENT

This invention was made with government support under NS107550 awarded by the National Institutes of Health. The government has certain rights in the invention.

BACKGROUND

Embodiments disclosed herein are directed to implantable sensory systems for use in restoring sensation, for instance, to the foot and/or hand of an individual.

By way of example, and not by way of limitation, the need to restore sensation in the foot may be in the setting of diabetic peripheral neuropathy. However, other conditions associated with sensory loss and/or pain in the extremity could also be the cause, for instance, these may include genetic disorders, peripheral nerve injuries, toxicities, neurodegenerative conditions, spinal cord injury, as well as other conditions. With respect to the hand and fingers, the need to restore sensation may be in the setting of paralysis, as one example.

Turning first to potential issues of loss of sensation in the foot, diabetes and its complications, as an example, provide major public health priorities and lower extremity complications are among the most debilitating and costly in diabetics. The prevalence of diabetes is expected to grow from the current estimates of about 425 million globally to more than 629 million by 2045. Distal Sensory Polyneuropathy (DSP) can occur in diabetic patients and is a length-dependent peripheral nerve injury that causes severe symptoms in about a quarter of people with type 2 diabetes, equating to nearly 10 million people in the US. Progressive DSP produces searing neuropathic foot pain in patients and results in gradual and profound loss of distal-predominant tactile sensation in patients' limbs and weakness that progresses to gait instability and falls. This in turn leads to formation of debilitating foot ulceration (DFU).

DSP affects both large fibers, associated with tactile signals of pressure and vibration, as well as small somatic fibers associated with noxious and thermal signals. Neuropathic pain is one of the most disabling symptoms, impacting about 20-30% of patients with diabetic neuropathy. In the absence of protective sensory feedback, diabetics experience abnormal plantar loading which leads to diabetic foot ulcerations. In particular, about 50% of DFUs develop at sites with elevated shear stress. The development of diabetic foot ulcerations leads to limb amputation. DFUs are present in about 28% of US Medicare beneficiaries. The annual cost of care for Americans with DFU is believed to exceed $25 billion annually. DFU can set in motion a cascade that progresses to mortality. After a limb is amputated due to diabetes, there is about a 50% 2-year probability that the other limb will be amputated. In addition, DFU is an independent risk factor for mortality within one year.

Despite the critical clinical need and DSP being a major complication of diabetes affecting millions of Americans, DSP has few existing treatment options and none directly address or restore loss of foot sensation. Known medications for reducing neuropathic pain have limited efficacy. Existing treatments for DSP also suffer from poor patient compliance.

Typically, management of DSP is restricted to pharmaceutical interventions. There are two medications that bear FDA labeling for neuropathic pain in diabetes: duloxetine and pregabalin. Off-label medications trialed in the course of the disease include tricyclic antidepressants, anticonvulsants, serotonin-reuptake inhibitors, and even opiates once the pain is intolerable. Patients with diabetes have notoriously poor medication compliance, with adherence rates as low as 36%. Likewise, externally donned devices suffer from poor patient compliance. DFU can be treated with devices, such as removable cast walkers, to offload plantar pressure. However, these devices were found to be used in only 28% of DFU patients' daily activities.

Turning to issues concerning loss of sensation in the hand and fingers, currently 5.4 million people in the United States (1.7% of the population) are paralyzed due to spinal cord injury (SCI), stroke and other causes. These survivors are often unable to perform basic activities of daily living and 85% lose their employment. Beyond lost wages, the lifetime cost of care for an individual with tetraplegia exceeds $2 million USD. Consequently, the financial burdens borne by families and the nation are substantial.

Significant resources have been devoted to developing brain-machine interface (BMI) technology to meet the needs of these individuals and decrease the burden of their care. The result has been a number of encouraging first-in-human studies demonstrating direct brain control of external devices including prosthetic (i.e., robotic) limbs. These robotic limbs can be equipped with sensors that mimic the mechanoreceptors of the skin and drive electrical stimulation of somatosensory brain regions to restore a basic sense of touch. However, despite nearly two decades of research, brain-controlled robotic arms have advanced only to early clinical trials, with some questioning the risk-benefit ratio of this approach.

An alternative approach is to reanimate one's own limb, rather than requiring a robotic arm designed for amputees. Indeed, patients prefer this strategy. In a survey of people with SCI, ~90% said they would be likely to adopt a BMI technology that restored grasping ability in their native hand, while fewer than 60% would adopt a technology that required a prosthetic hand. In response, pioneering work has demonstrated restoration of basic arm and hand movements using brain-controlled functional electrical stimulation (FES) of paralyzed muscles. Drawing on earlier work in non-human primates, a group at Ohio State University and Battelle recently used cortical multiunit activity to drive functional electrical stimulation of paralyzed extrinsic hand muscles. The subject was able to control hand movements to grasp and release objects. In parallel, a team at Brown University and Case Western Reserve University used motor cortex activity to drive reach and grasp movements in a paralyzed subject.

Direct motor control of paralyzed arms is a fundamental shift in rehabilitation strategies. These recent results validate the treatment strategy. However, they also expose a critical barrier to further progress: the lack of somatosensory feedback from the hand.

Somatosensation is required for even basic hand control. The above studies underscore this fact. The grasping behaviors performed with the insensate hand were well-below the required minimal required dexterity for activities of daily living and required constant visual attention to guide movements. This is an expected finding as vision without tactile feedback provides no guidance concerning grip force, slip, and vibration (i.e., tactile perception) required for finger function.

SUMMARY OF THE INVENTION

In one aspect, an implantable sensory system is provided. The system includes at least one force sensor implanted subcutaneously within a hand or foot of a patient and a base unit worn by the patient or implanted subcutaneously. The at least one force sensor is configured to transmit wireless communication signals to the base unit in response to forces sensed by the at least one sensor, and the base unit is configured to transmit sensory data to a separate neural implant or to apply peripheral nerve stimulation to the tibial nerve. According to at least some embodiments, the at least one force sensor is configured to transmit the wireless communication signals to the base unit by magnetic human body communication (mHBC).

According to another aspect, an implantable sensor device is provided. The sensor device includes a force sensor for being implanted subcutaneously within a patient and being configured to transmit wireless communication signals in response to and concerning forces sensed thereby. According to at least some embodiments, the force sensor is configured to transmit the wireless communication signals via magnetic human body communication (mHBC) such that information of tactile sensations measured by the force sensor is transmitted in via the wireless communication signals. The force sensor may be configured to sense normal and shear components of forces experienced by the hand or foot of the patient. In addition, the force sensor may be a battery-less capacitive pressure sensor microfabricated within a biocompatible, hermetically sealed fused silica package containing an application-specific integrated circuit.

According to a further aspect, a method of transmitting tactile sensations is provided. The method includes transmitting wireless communication signals from at least one force sensor implanted subcutaneously within the hand or foot of the patient to a base unit worn by or implanted subcutaneously in the patient. The at least one force sensor is configured to transmit the wireless communication signals to the base unit by magnetic human body communication (mHBC).

Other aspects of the invention will be readily apparent from the following detailed description.

BRIEF DESCRIPTION OF THE DRAWINGS

FIG. 5 is a plan view of a sensor according to an embodiment.

FIG. 6 shows the general size of the sensor of FIG. 5.

FIG. 7 is an exploded view of a part of the sensor of FIG. 5.

FIG. 8 is a schematic view of the implantable foot sensory system according to an embodiment.

FIG. 20A is a microphotograph of an implantable CMOS chip sensor according to an embodiment.

FIG. 20B is a schematic diagram of an implantable CMOS chip sensor according to an embodiment.

FIG. 20C is a microphotograph of a PCB for the CMOS chip and force sensor according to an embodiment.

FIG. 20D is a microphotograph of a force sensor according to an embodiment.

FIG. 20E is a plot of measured frequency shift of the on-chip oscillator versus applied normal force on the capacitive force sensor.

FIG. 20F is a schematic view showing shear force sensing.

FIG. 20G is a schematic of an integrated dual oscillator in a CMOS chip according to an embodiment.

FIG. 20H is a diagram showing the frequency shift of the tow integrated oscillators when shear forces are applied.

FIG. 21 is an image showing magnetic induction powering in which the body acts a communication channel.

DETAILED DESCRIPTION OF THE INVENTION

Definitions

Figures 1, 2, 3, 4:
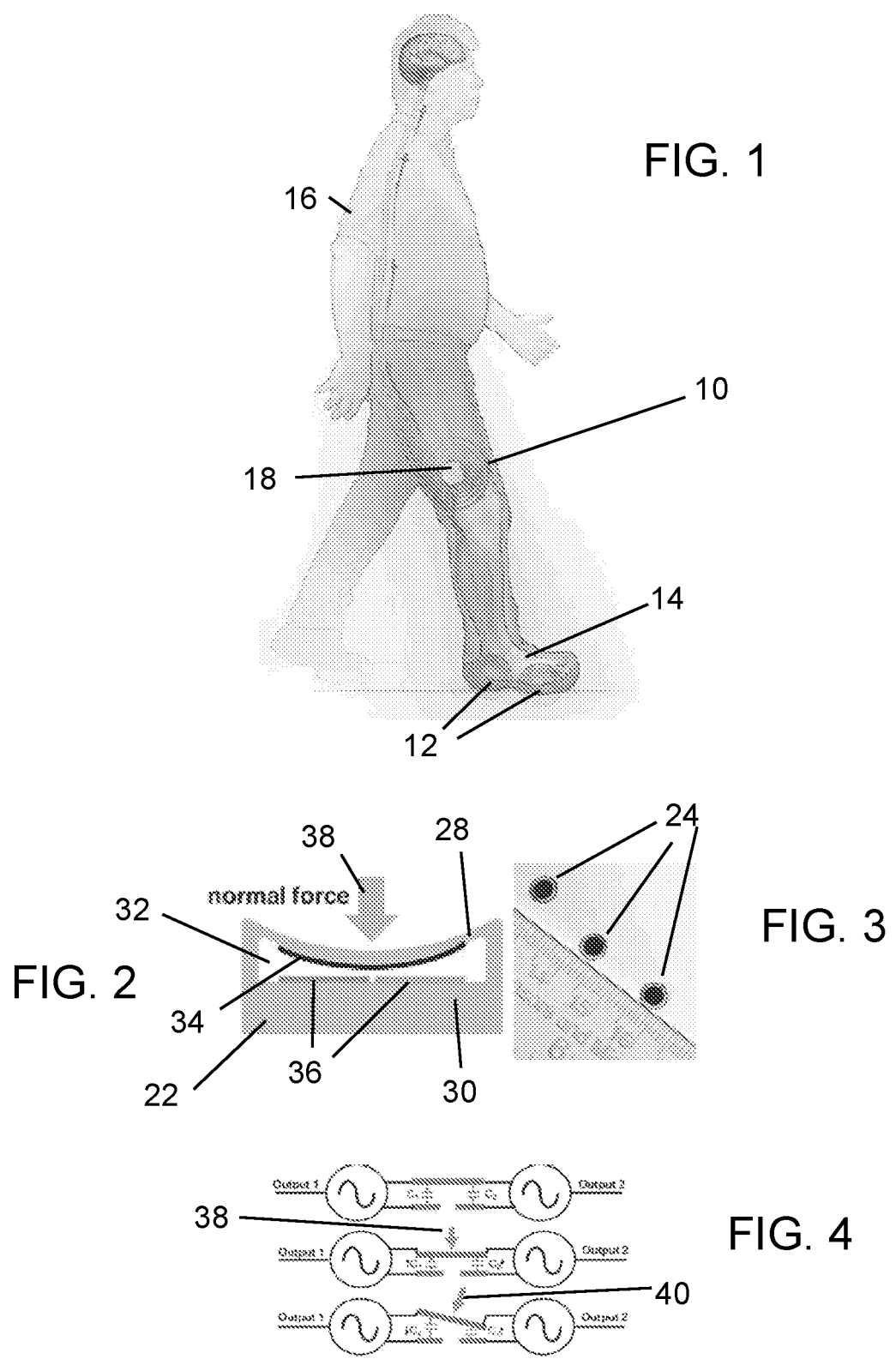
FIG. 1 is a view showing an implantable foot sensory system implanted in a patient according to an embodiment.
FIG. 2 is a schematic diagram of an implantable sensor according to an embodiment.
FIG. 3 is a view generally showing the size of an implantable sensor according to an embodiment.
FIG. 4 is a schematic diagram showing operation of an implantable sensor according to an embodiment.

The following definitions are provided. It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

As used herein, a "subject" or "patient" is a mammal, e.g., a human, mouse, rat, guinea pig, dog, cat, horse, cow, pig, or non-human primate, such as a monkey, chimpanzee, baboon, or gorilla. In one embodiment, the patient is a human.

Unless defined otherwise in this specification, technical and scientific terms used herein have the same meaning as commonly understood by one of ordinary skill in the art and by reference to published texts, which provide one skilled in the art with a general guide to many of the terms used in the present application.

Implantable Foot Sensory System

According to embodiments disclosed herein, a new treatment approach is provided and intended to have a major impact on the health of millions of individuals suffering from the effects of distal sensory polyneuropathy (DSP). The approach is based on sensor-informed peripheral nerve stimulation (PNS) using a minimally invasive, wireless, implantable device that activates nerves of the leg in response to plantar pressure. The peripheral nerve stimulation is provided as therapy to reduce neuropathic pain and restore foot sensation. In addition to the therapy disclosed above, embodiments disclosed herein may have broad significance as a closed-loop bioelectronic medical device utilizing wireless, chip-based sensor nodes that provide a modular and scalable technology platform for providing many other therapies for treating different ailments.

According to one contemplated embodiment, an implantable foot sensory system and method are provided that: (1) detect normal and sheer forces from the subdermal space of the plantar surface of the foot of the patient using a passive (battery-less), capacitive force sensor; (2) transmit force data to an implanted base unit located in the proximal leg via magnetic human body communication; and (3) translate this data into stimulation triggers or pulses to activate the tibial nerve.

Thus, the system may be composed of two implantable components: one component consists of miniature sensors that are implanted subcutaneously on the planar surface of the foot that will sense pressure. These sensors wirelessly transmit signals in response to foot pressure via magnetic human body communication (mHBC) to the second component: a base unit that is implanted subcutaneously in the lateral thigh with an integrated nerve cuff lead that targets the tibial nerve. The base unit is battery-powered and can modulate neural stimulation in response to sensor output. Together, these two components form a closed-loop system that transmit tactile sensations from the planar surface of the foot to the tibial nerve near the knee. The capacity for PNS to reduce neuropathic pain and produce foot sensations should enable this system to improve current standards of therapy.

In absence of regular PNS stimulation from healthy nerves, the brain perceives noise from peripheral nerves. For example, phantom nerve pain baseline sensory nerve volleys are perceived as pain. The technology disclosed herein aims to recreate normal sensory conduction via the tibial nerve. This replaces the missing signals that are normal due to PNS damage during diabetes. The brain needs contextual information for the sensory signals, which makes behavioral sense. Ulcers are created because of pressure on foot for long periods of time. The patient receives no somatosensory feedback. However, with embodiments disclosed herein, such patients will now be able to receive somatosensory feedback. This recreates a healthy afferent sensory signal to the brain reducing the effect of aberrant pain sensory signaling and resulting in the diabetic user moving their foot when it is feeling pressure, reducing the instances of ulcers, and resulting amputation.

Accordingly, a treatment for DSP is based on an implantable system for plantar pressure sensing and closed-loop peripheral nerve stimulation. The closed-loop configuration provides peripheral nerve stimulation (PNS) in response to plantar pressure sensed by miniature subcutaneous sensors in the sole of the foot of the patent thereby restoring foot sensation and reducing pain. The sensors reliably report normal and shear components of the ground reaction forces experienced during standing and walking based on sensitivity to tactile stimuli acting on the sole of the foot of the patient. The battery-less capacitive pressure sensors may be microfabricated within a biocompatible, hermetically sealed fused silica package containing an application-specific integrated circuit (ASIC). The ASIC functions to wirelessly transfer sensed normal and shear stresses through a magnetic human body communication (mHBC) channel to a subcutaneous base unit in the thigh. In turn, the battery-powered programmable base unit modulates neural stimulation parameters in response to the sensors output and delivers stimulation through an integrated nerve cuff lead.

Artificial activation of somatosensory neural pathways using electrical stimulation and the use of targeted peripheral nerve stimulation (PNS) provide effective methods for relieving diabetic neuropathic pain. In addition to pain, PNS of the tibial and common peroneal nerves near the knee can be effective at restoring foot sensation and improving gait stability of the patient. Thus, the closed-loop PNS device disclosed herein is effective in both reducing neuropathic pain and producing foot sensations. Accordingly, PNS is used to achieve a complete therapy that is significantly more effective than known pain medication alone.

As shown in FIG. 1, the system 10 includes multiple, separate, miniature subcutaneous sensor devices 12 implanted subcutaneously on a plantar surface of the sole of a numb foot 14 of a DSP patient 16. The sensor devices sense plantar normal and shear stresses and transmit the data wirelessly to an implantable pulse generator or base unit 18 to drive electrical stimulation of peripheral nerves near the knee. The base unit 18 may be implanted subcutaneously in the lateral thigh of the patient 16 and have an integrated nerve cuff lead targeting the tibial nerve near the knee and may be configured to provide modulated PNS to the tibial nerve via an integrated nerve cuff electrode 20 (see FIGS. 8 and 9). Thus, this embodiment provides a neuroprosthetic device that is minimally invasive, with components (other than the nerve cuff 20) placed just under the skin and without any interconnecting wires. As shown in FIG. 1, given that the components of the system are entirely implanted, the system requires no donning by the patient 16.

The miniature subcutaneous sensor devices 12 may include capacitive pressure sensors 22 microfabricated within a biocompatible, hermetically sealed fused silica package 24 that contains an application-specific integrated circuit (ASIC) 26. For instance, see FIGS. 2-7. The ASIC 26 transmits sensor data wirelessly to the base unit 18 using magnetic human body communication (mHBC). The mHBC may also be used to provide power from the battery-powered base unit to the sensor ASIC 26. Thus, the sensor devices 12 are able to sense plantar loading conditions and communicate with the base unit 18 while maintaining the minimally invasive nature of sensor implantation within the sole of the foot.

An example of a capacitive fused silica pressure sensor 22 is best shown in FIG. 2. The sensor 22 comprises two fused silica layers which include an upper silica plate 28 and a lower silica substrate 30 with a cavity 32 located therebetween. A circular upper electrode 34 is formed on the upper silica plate 28 facing the cavity 32, and multiple electrodes 36 are formed on the lower silica substrate 30 facing the cavity 32. The cavity 32 acts as an air gap between the upper and lower electrodes. The upper plate 28 is bonded to the lower substrate 30 utilizing a laser-assisted, simultaneous localized fusion bonding and dicing technology. Using four, rather than two, lower electrodes 36 allows the simultaneous measurement of both normal and shear forces. In addition to normal and shear sensing capability, CMOS integrated circuits may also be encapsulated within the fused silica sensor (such as the ASIC 26 referenced above).

As shown in FIG. 2, an externally applied normal force 38 causes deflection of the upper fused silica plate 28, thereby changing the capacitance between the upper electrode 34 and each of the lower electrodes 36 supported by the lower fused silica plate 30. FIG. 4 shows quadrant-based multi-electrode capacitive readout for simultaneous normal and shear force measurement within a single sensor 22. As shown in FIG. 4, the capacitance between the electrodes remains constant when no force is applied to the sensor 22 (see condition shown at top of FIG. 4). If a normal force 38 is applied to the sensor 22, then the capacitance between the upper electrode 34 and each lower electrode 36 increases (see condition shown in middle of FIG. 4). If a sheer force 40 is applied to the sensor 22, then the capacitance between the upper electrode 34 and at least one of the lower electrodes 36 increases and the capacitance between the upper electrode 34 and at least one of the lower electrodes 36 decreases (see condition shown in bottom of FIG. 4).

The relative size of the fused silica sensors 22 may be as shown in FIG. 3 relative to a mm-scaled ruler. For purposes of example, and not by way of limitation, a sensor 22 may have a diameter of about 5 mm, a deflecting upper silica plate thickness of about 200 μm, and an overall thickness of about 700 μm. This sensor may show a 2× capacitance excursion over the range 0-10 N of applied normal force when placed within a silicone skin phantom and can function under both static and dynamic loading. However, the dimensions of the sensor can be altered as needed or desired. For instance, the sensors 22 may need to take into account large normal forces that may be encountered in a foot sensor application. Finite element modeling of the sensor and its comparison to experimentally measured data confirmed that the sensor load-deflection behavior can be described by the analytical model $w_O=pa^4/64D$, where "$w_O$" is the plate deflection at the center of the sensor, "p" is the normal-directed load per unit area applied to the sensor, "a" is the radius of the deflecting portion of the upper plate, and "D" is the flexural rigidity of the upper plate (which is proportional to the cube of its thickness). Thus, the sensitivity of the sensor can be adjusted by the ratio a4/t3. These high powers of geometric parameters give great flexibility in sensor design.

Consider a sensor 22 designed for a 220 lb (100 kg) patient, standing on one foot with all weight placed on a single sensor within that foot (a worst-case scenario). This represents an approximately 100× force increase over the 10 N sensors referenced above. Scaling the sensor by a factor of 0.56 (i.e., decreasing the radius of the deflecting silica plate by 56% and increasing its thickness by 56%), yields the requisite 100× increase in stiffness. These geometric variations can be achieved by current sensor fabrication technology (including ASIC 26 encapsulation within the sensor 22). It should further be noted that additional stresses (the patient jumping, the patient carrying loads) would not result in sensor failure, as the sensor can be intrinsically protected from an overforce condition by its ability to operate in touch mode, where upper and lower silica plates touch (electrode shorting in touch mode is prevented by a thin insulation layer (not shown) deposited over the electrodes during fabrication).

There is a tradeoff between the requirements of scaling the sensor size down to achieve the pressure range requirements and requiring a relatively large sensor area for RF communication with the base unit. RF coils 42 for communication may be placed within the sensor cavity 32. Should achieving these conflicting goals be challenging, the overall sensor diameter may be held large (e.g., 5 mm), and the sensor cavity 32 may be separated (e.g., by stops or walls etched into the fused silica) into a non-deflecting, large diameter region housing the RF coils, and a smaller diameter, deflecting region containing the sensing capacitors. Alternatively, the sensors can be of a relatively large diameter and operated in touch mode, in which case the reduced sensitivity of touch mode operation can be compensated by increased ASIC gain.

Referring to FIG. 8, a top-level diagram of the different components and wireless communication links within the system 10 is provided. Within the base unit 18, a Bluetooth enabled ultra-low power microcontroller 44 (such as a WC7220B0 microcontroller), an ASIC 46, and an accelerometer device 48 are mounted on a printed circuit board 50. The ASIC 46 wirelessly communicates with sensors 22 through a mHBC link 52. A coil 54 of the base unit 18 transmits a carrier signal to the sensors 22 and receives backscattered signals from the sensors 22 (corresponding to the measured force vector from each sensor 22) and routes these signals to the microcontroller 44 after processing and conditioning by the ASIC 46. The ASIC 46 communicates in this manner with multiple sensors 22 through the use of different frequency channels. The microcontroller 44 receives the conditioned force vectors from ASIC 46 and sends stimulation commands to the ASIC 46 which then generates charge-balanced current-controlled pulses based on commands from the microcontroller 44 to drive the off-package nerve cuff 20 to stimulate the peripheral nerve 56 of the patient.

The microprocessor 44 can also be configured to wirelessly communicate with an external unit 58 via a Bluetooth low energy (LE) wireless communication link 60. The external unit 58 may be used, for instance, to control operation of the base unit 18 and monitor information passed between the sensors 22 and the base unit 18. The microcontroller 44 can operated in a hibernate (sleep) mode to reduce power consumption to under 1 μW. A watch dog timer of the base unit 18 may wake up the Bluetooth LE receiver every 50 ms for 100 μs to look for any new command issued by the external unit 58. The output of the accelerometer device 48 may also communicate to the external unit 58 via Bluetooth LE wireless communications.

One or more batteries 62, such as three 3.7V 400 mAh Lithium Ion batteries, may be placed on top of the PCB 50 without covering the on-chip Bluetooth antenna (not shown) within the microcontroller 44. Merely for purposes of example, all components and devices (except for the off-package nerve cuff 20) may be designed to fit within a cylindrical housing, for instance, with a base diameter of about 60 mm and height of about 10 mm.

As shown in FIG. 8, each sensor unit 22 includes the ASIC 26, the force sensor 22, and a sensor coil 42, all encapsulated within the fused silica sensor package 24. The battery-less ASIC 26 of the sensor device 22 may use the sensor coil 42 to receive the carrier signal sent by the base unit 18 through the mHBC link 52 and harvest energy therefrom required to run a few active blocks. The ASIC 26 is configured to read the force sensor capacitance, modulate the received carrier signal by the measured force information, and send the modulated carrier back to the base unit 18 through the mHBC link 52 using the sensor coil 42.

Figure 9:
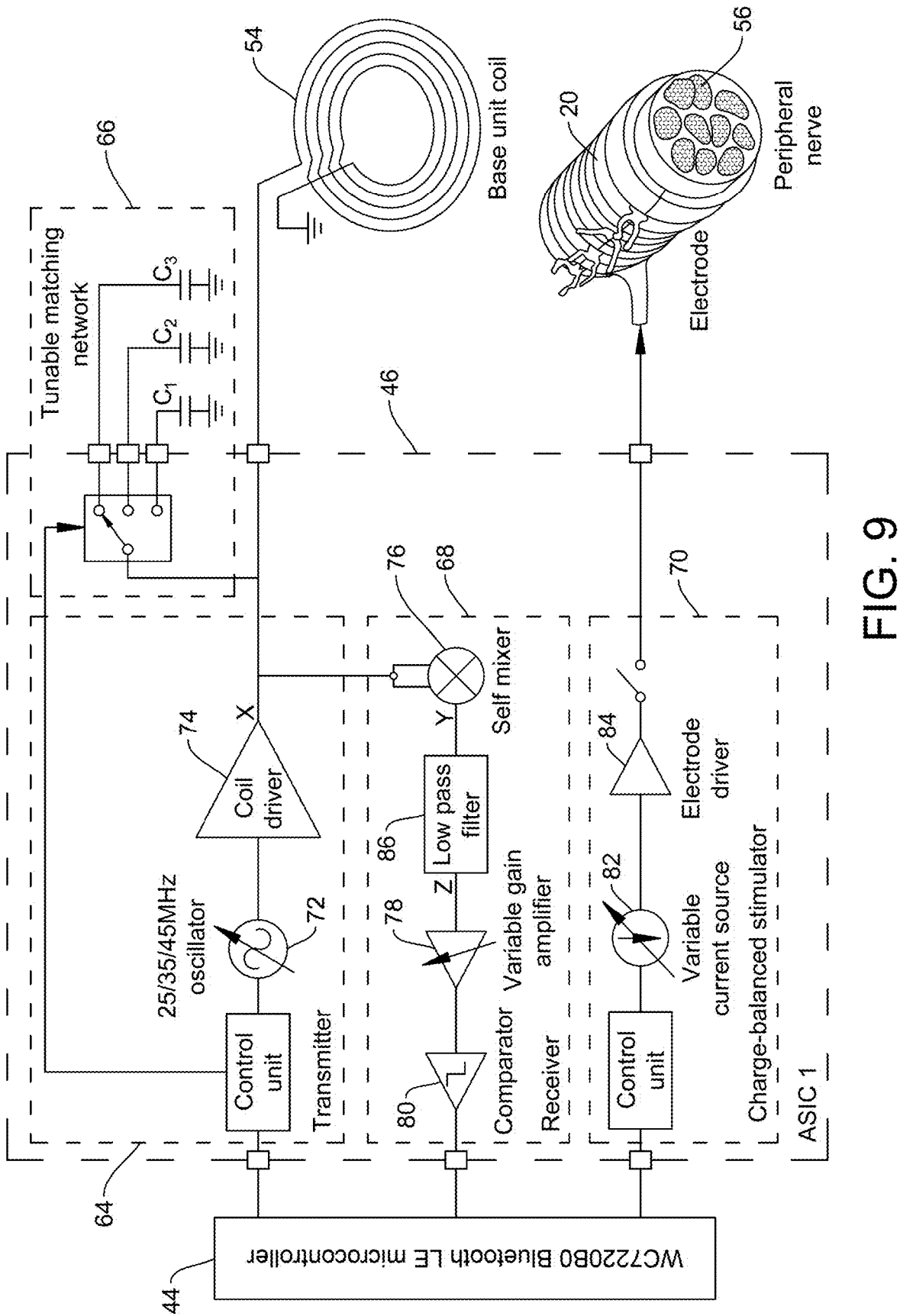
FIG. 9 is an electronic schematic view of the base unit of the implantable foot sensory system according to an embodiment.

Referring to FIG. 9, a block diagram of the ASIC 46 of the base unit 18 provides an embodiment in which the ASCI 46 forms the core of the base unit 18. As shown in FIG. 9, the ASIC 46 may have a transmitter unit 64, a tunable matching network unit 66, a receiver unit 68, and a charge-balanced stimulator unit 70. As an example, in order to communicate with three separate sensors 22, the ASIC 46 can be configured to operate at three different carrier frequencies of, for instance, 25 MHz, 35 MHz, and 45 MHz (i.e., the coil of each of the three sensors 22 is tuned to one of these frequencies). A tunable voltage controlled oscillator (VCO) 72 may be implemented within the transmitter unit 64 that can be tuned to any of these frequencies by the microcontroller 44.

A coil driver 74 is interconnected to the VCO 72 to drive the combination of the tunable matching network unit 66 and the base unit coil 54. The tunable matching network 66 connects an off-chip capacitor across the coil 54 to create a resonance around the carrier frequency of interest. For example, to communicate with a first sensor, the microcontroller 44 sets the frequency of the VCO 72 to 25 MHz and uses the tunable matching network unit 66 to connect the corresponding capacitor across the coil 54 to shift the resonance frequency of the coil 54 to 25 MHz aligning it with the carrier.

Figure 10A:
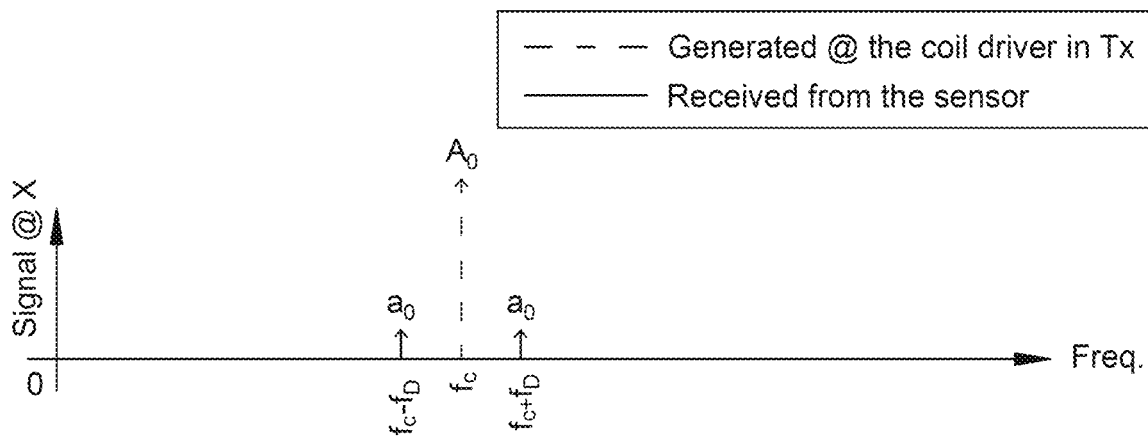
FIG. 10A is a diagram showing a frequency spectrum of signals received at the input of the integrated circuit of the base unit according to an embodiment.
Figure 10B:
FIG. 10B is a diagram showing a frequency spectrum of the signals after having been self-mixed and filtered by the integrated circuit of the base unit according to an embodiment.

At the input of the receiver 68 within the ASIC 46, the small back reflected carrier signal modulated with the force information from the sensor 22 is combined with the large carrier signal at the output of the coil driver 74 (point X in FIG. 9). A typical spectrum for this case (at point X) is shown in FIG. 10A, where fc and fD represent the carrier frequency and the modulating frequency (corresponding the sensor readout), respectively. To significantly improve the sensitivity of the receiver unit 68, the input stage of the receiver unit 68 is a self-mixer 76 used as a correlator effectively realizing a matched filter. In this case, the sum of the large signal carrier and small signal received modulated carrier is squared in the self-mixer 76 (self-multiplier). The self-mixer output (point Y in FIG. 9) contains several frequency components at f, fc, $2f \pm fD$, and $2fc \pm 2fD$ as shown in FIG. 10B. A low-pass filter can be used to remove all undesired components detecting the desired frequency, fD, at the filter output (point Z in FIG. 9). The filter output is further amplified using a variable gain amplifier 78 and converted to a square wave using a comparator 80 and sent to the microcontroller 44.

Figure 11:
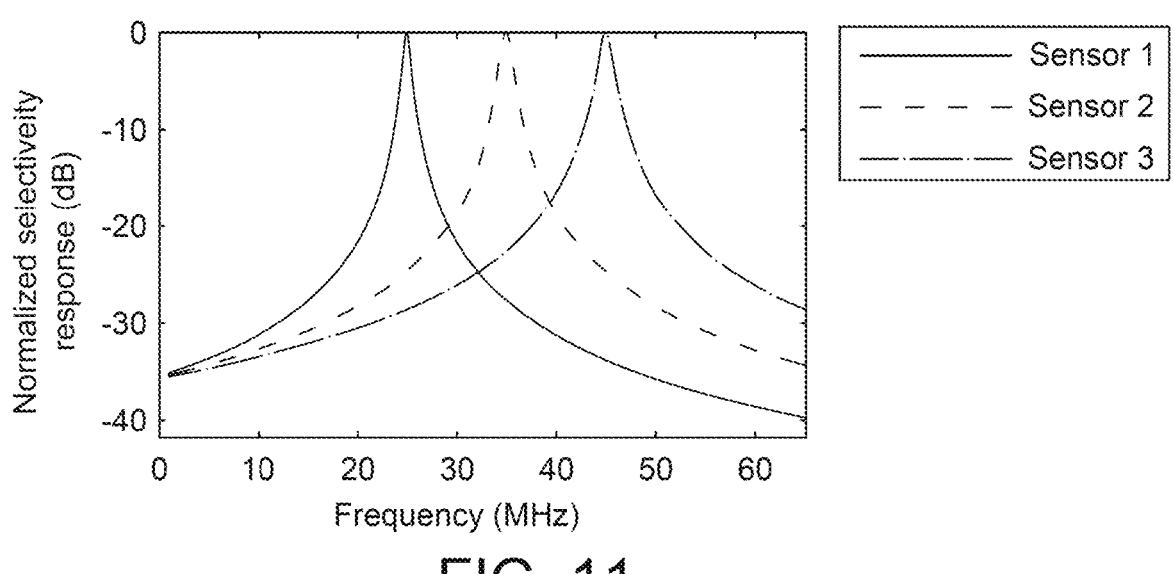
FIG. 11 is a diagram showing three communication bands between the base unit and three separate sensors according to an embodiment.

Based on the measured and transmitted force vector by the sensor 22, the microcontroller 44 generates control signals for the ASIC 46 to perform charged balanced stimulation via the nerve cuff 20. The design of the charge-balanced stimulation circuit 70 within the ASIC 46 consists of variable current sources 82 and electrode driving circuitry 84. FIG. 11 shows an example of the spectrum for three operating bands at the output of the ASIC 46.

Measurements for a matching network for mHBC coils indicate that a quality factor of about 45 can be achieved.

Using this quality factor, the communication bands around 25 MHz, 35 MHz, and 45 MHz are considered for mHBC links 52 with the three sensors 22 (one band per sensor) to ensure better than 25 dB band-to-band isolation making the cross-talk between the back reflected signals from different sensors negligible. The low-pass filter 86 in the receiver unit 68 of the ASIC 48 further suppresses any cross-talk between the transmitted signals from the sensor units 22. The ASIC 46 sequentially (about every 60 ms) switches between these three bands to communicate with individual sensors 22.

Figure 12:
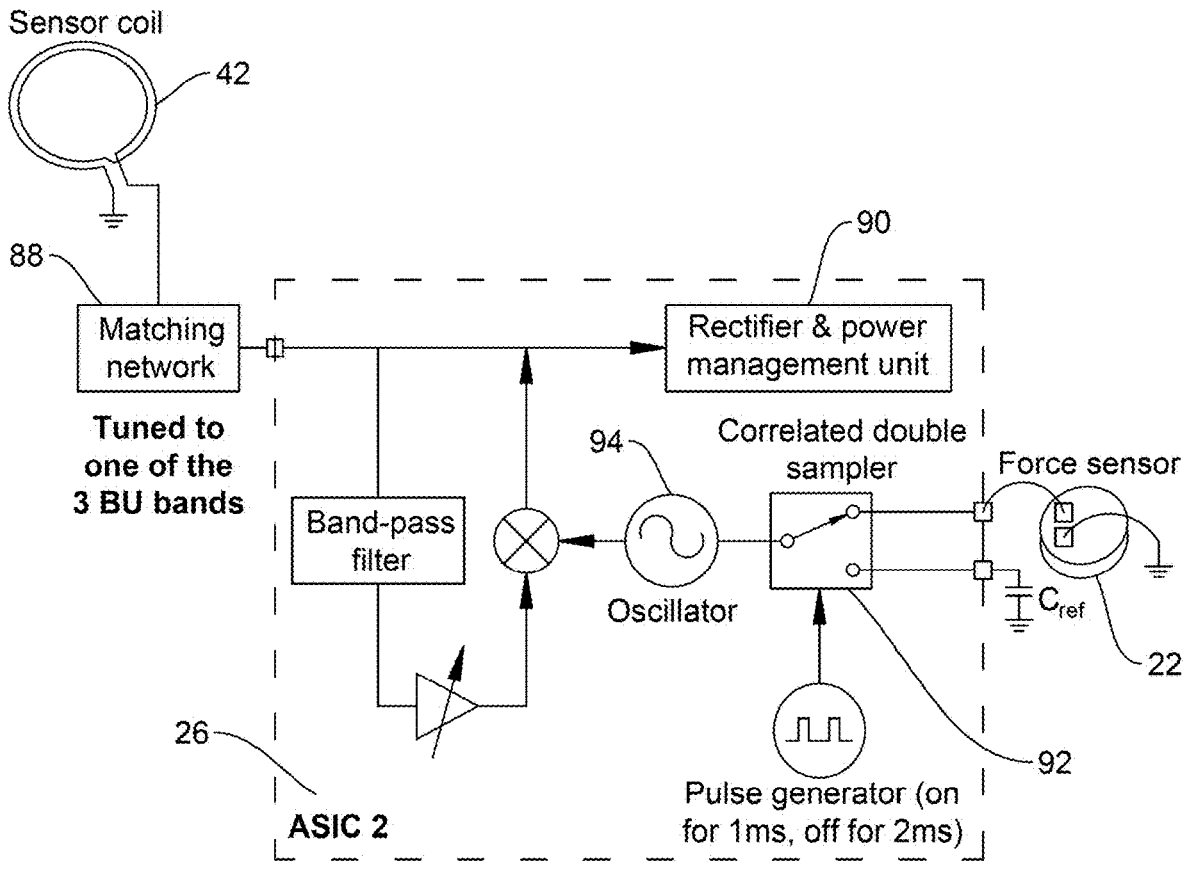
FIG. 12 is a block diagram of an application-specific integrated circuit (ASIC) within each sensor unit according to an embodiment.

An example of a block diagram of the ASIC 26 within each sensor unit 22 is proved in FIG. 12. The carrier signals transmitted from the ASIC 46 in the base unit 16 is received using the sensor coil 42. A matching network unit 88 connected to the coil 42 is used to tune the coil 42 to one of the communication bands (i.e., 25 MHz, 35 MHz, and 45 MHz, for sensors 1, 2, and 3, respectively). The received signal at the output of the matching network unit 88 is used for power harvesting using a rectifier and power management unit 90. The power management unit 90 is used to power a few active devices within the ASIC 26. An ultra-low power correlated double sampling capacitance-to-time converter 92 is used within the ASIC 26 to read the capacitance of the force sensor 22. In this case, the force sensor capacitor and a reference capacitor are swapped sequentially within a relaxation oscillator 94 to eliminate any process variation and mismatches. A low power clock is used to perform the sequential swap such that the capacitive sensor is read for 2 ms and the reference capacitor is read for 1 ms. Within each readout period, the frequency of the relaxation oscillator 94 (which is <3 MHz) represents the capacitance value. The received carrier signal at the output of the matching network unit 88 is then amplitude modulated with the output of the relaxation oscillator 94 using a frequency mixer, creating side bands at $fc \pm fD$, where fD corresponds to the measured value of the capacitive sensor for 2 ms and the known reference capacitor for 1 ms. Given the readout time of 60 ms per sensor, twenty measurements for capacitive force sensor and twenty measurements for the reference capacitor may be performed, which is then used to reduce the effect of noise through averaging. The modulated carrier is routed back to the sensor coil 42 and back transmitted to the base unit 18 through the mHBC link 52.

By way of example, and not by way of limitation, simulations show a power consumption of less than 80 μW for the ASIC 26 when in use. Also, for a 6V stimulation voltage across a ~2 k$_A$ electrode, considering an estimated mHBC average loss of 22 dB around the frequency band of interest (given the distance between the base unit 18 and sensors 22), a desired 1.2V supply voltage harvested for the ASIC 26, an estimated power consumption of 250 μW for the receiver and transmitter units, 68 and 64, within the ASIC 46, and an active power consumption of ~10 mW for the microcontroller 44 (when Bluetooth LE is in use), the 1.2 Ah energy available from the batteries 62 within the base unit 18 results in about 98 hours of operation (i.e. concurrent sensor read-out, mHBC communication, stimulation, and Bluetooth communication) before the batteries 62 may require recharging.

Figure 13:
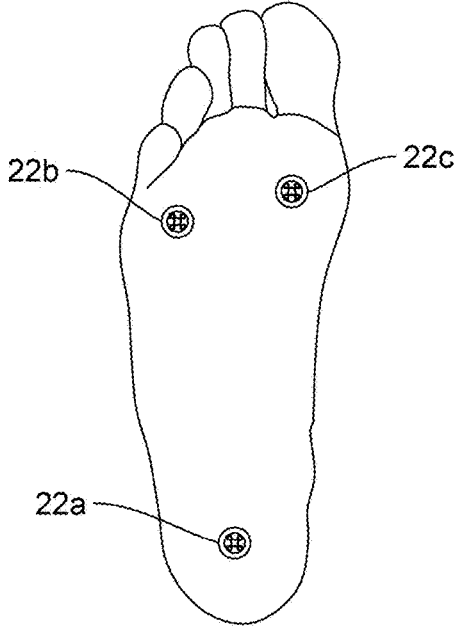
FIG. 13 is a view showing an example of the placement of three sensors relative to a foot of the patient according to an embodiment.

By way of example, FIG. 13 shows potential subdermal implant locations of three sensors implanted within a foot of a patient. For instance, sensor 22a may be implanted in the heel of the foot, and sensors 22b and 22c may be implanted laterally on opposite sides of the ball of the foot. With this arrangement, how the foot is contacting a ground surface can be determined based on data of the forces being exerted on each of these regions of the foot.

Figure 14:
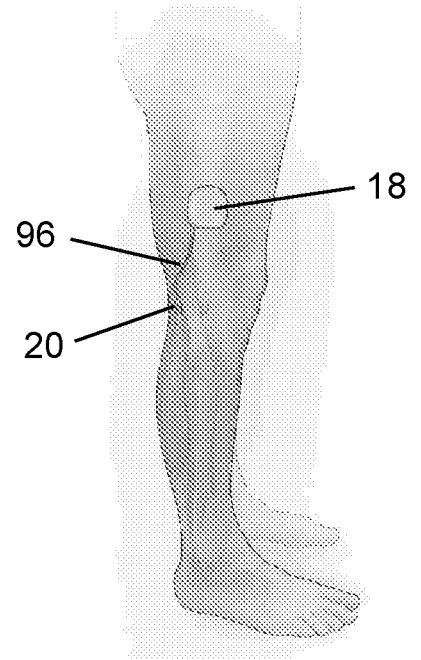
FIG. 14 is a view showing an example of the placement of the base unit adjacent the knee of the patient according to an embodiment.
Figure 15:
FIG. 15 is an image of a peroneal nerve of a human patient on which an electrode may be placed.

FIG. 14 shows an example of the implant location of the base unit 18 within an outer thigh of the patient's leg slightly above the knee of the patient. A lead 96 extends from the base unit 18 to the nerve cuff 20. FIG. 15 shows an example of the common peroneal nerve near the knee to which the nerve cuff 20 and stimulations may be applied.

The accelerometer unit 48 of the base unit 18 may be a three-axis accelerometer used to provide a signal of subject movement that can be used to refine the function of the system 10. For instance, the system 10 may be configured to have a low-power standby mode, to save battery power when the subject is resting, and an active mode when the closed-loop PNS is engaged. Accelerometry may be used to provide "wake-up" and "shut-down" signals to the system 10 to transition between standby and active modes. In addition, acceleration signals may be used to infer gait kinetics as a supplement to the plantar sensors 22. The use of machine learning, using both pressure and acceleration data as inputs and force plate data as the output, may be used to improve the ground reaction force estimates provided by the system 10. The ASIC 46 on the base unit 18 may be designed with the capacity to perform inference based on machine learning models trained offline.

As discussed above, due to lack of treatments, most care focused on prevention of DSP is through glycemic control and lifestyle management (i.e., exercise and dietary modification). Unfortunately, there is little evidence that either of these preventative strategies can effectively reduce neuropathic pain once established. Given the high burden of the disease, the embodiments discussed above provide a bold new treatment option for DSP. The implantable neuroprosthesis is an innovative treatment strategy for both pain and sensation. This strategy is a substantial departure from current pharmacotherapy that focuses only on pain and not on the loss of sensation that leads directly to DFU.

In addition to the treatment innovation, the proposed neuroprosthetic device has an innovative design that may benefit medical device technologies for other diseases. The use of microfabricated fused silica for the sensors has a myriad of benefits. It provides a hermetic and biocompatible package suitable for chronic implantation and transparency to electromagnetic radiation to support wireless operation. In addition, the mHBC scheme for wireless operation is novel in the context of implantable devices. The relatively low path loss magnetic fields can provide the sensor ASIC both power and a means to communicate the pressure data via backscattering.

With regard to clinical treatment, the proposed strategy offers a new and substantively different approach. By intervening with a plantar pressured-based therapy prior to foot ulceration, rather than after as with offloading boots, the aim is to curtail the devastating cascade of morbidity and mortality set in motion once ulcerations have occurred.

With regard to clinical technology, the closed-loop PNS system of the embodiments could provide new options for treatment of disease with bioelectronic medicine. Chip-based wireless sensors of the disclosed embodiments remove any requirement of co-localizing the sensor and stimulator. This may be particularly beneficial in applications requiring widely separated or easily replaceable implanted sensors. It will be useful when long implanted cables would otherwise be required, particularly if spanning joints, where mechanical fatigue and tissue irritation is likely.

Further, as alternatives to the implanted sensors and base units discussed above, a less invasive treatment option may be to utilize the sensors and/or the base unit as a wearable device. This could be used in conjunction with percutaneous or transcutaneous PNS.

Implantable Hand/Finger Sensory System

The dexterous hand is a defining feature of human existence. Paralysis robs an individual of this humanizing characteristic by disrupting neural communication between the brain and body. Emerging brain-machine interface (BMI) technologies have shown promise at restoring top-down communication in the form of brain controlled functional electrical stimulation (FES) of paralyzed arm muscles. Yet, somatosensory feedback, which is essential for movement control, is missing.

Embodiments disclosed herein provide an implantable, hermetically-sealed finger sensor, a flexible circuit worn at the wrist, and a methodology of wireless device communication. The finger sensor is uniquely tuned for forces realized at the fingertip (low newton sensitivity) and it pairs with a flexible circuit system worn at the wrist like a watch band, wrist band, or the like.

Figure 16:
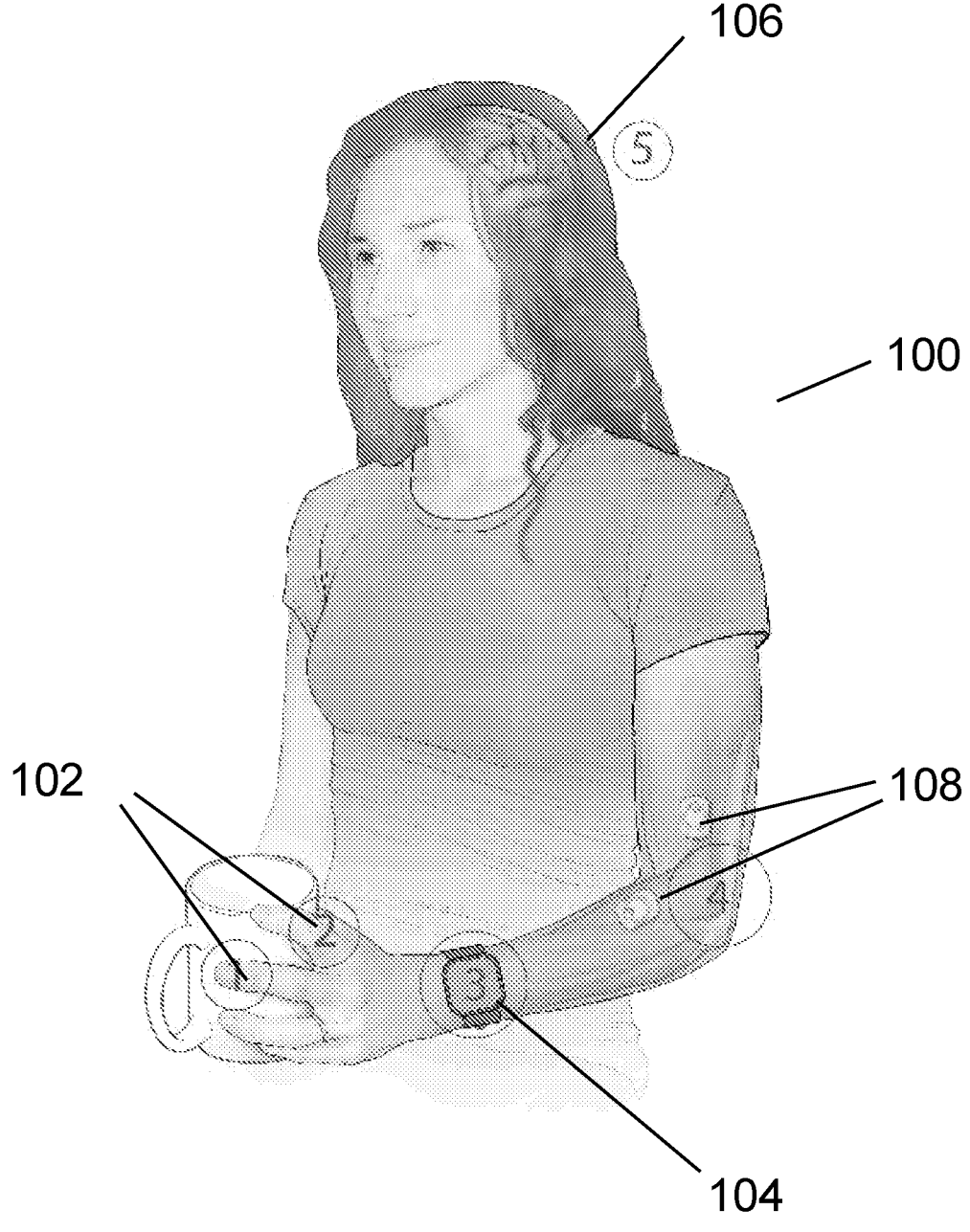
FIG. 16 is a view showing an implantable hand/finger sensory system on a patient according to an embodiment.
Figure 17:
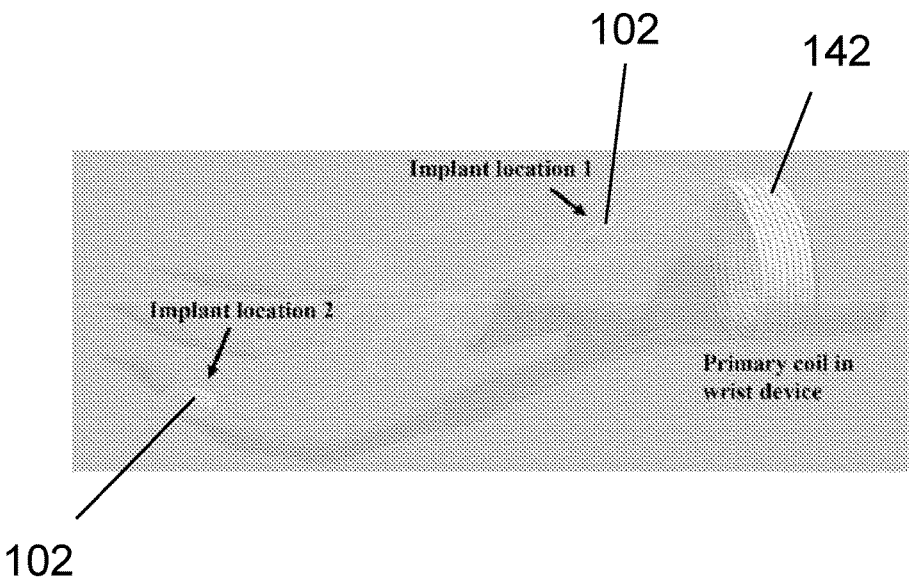
FIG. 17 is a view showing an example of the placement of two sensors relative to a hand of the patient according to an embodiment.

By way of example, FIG. 16 discloses an embodiment of a reanimation system 100. Implanted hand/finger sensors 102 relay force data to a wrist receiver 104. Neural implants 106 encode this sensory data and decode motor intent to drive muscle stimulators 108. FIG. 17 discloses potential locations for the implanted sensors 102 and shows their proximity to the wrist receiver 104 worn externally as a band about the wrist.

The implantable tactile sensor 102 for the finger measures forces acting on the skin and wirelessly conveys this information via the wearable hub 104 to the brain where somatosensory feedback is encoded with stimulation. The subcutaneous force-sensing device 102 includes of a capacitive sensor 110 whereby forces acting at the skin surface cause changes in the inter-plate distance resulting in measurable capacitance changes (similar as described above for sensors implanted in the foot). The capacitor plates 122 and 126 are housed on silica substrates 114 which when fused together provide a hermetic package (see right side of FIG. 18). Signal processing of the capacitance changes and wireless transmission of the data to a base unit 104 worn on the wrist is accomplished by an application-specific integrated circuit (ASIC) 116 bonded to the plates in the package. See FIG. 18. The ASIC 116 is powered wirelessly from the battery-powered base unit (i.e., Hub) 104 using near-field energy harvesting via an antenna coil 118.

According to an embodiment, the Hub 104 consists of a flexible circuit that is worn at the wrist and may be, for instance, embedded in a wristwatch or the like.

According to an embodiment, the targeted size of the sensors 102 may be about 5-mm in diameter and 2-mm thick, with a form factor ideal for human use. This size is compatible with implantation below the glabrous skin of the palm, including thenar, hypothenar, and metacarpal pads. Force is directed at these palmar sites during natural power grasping.

Figure 18:
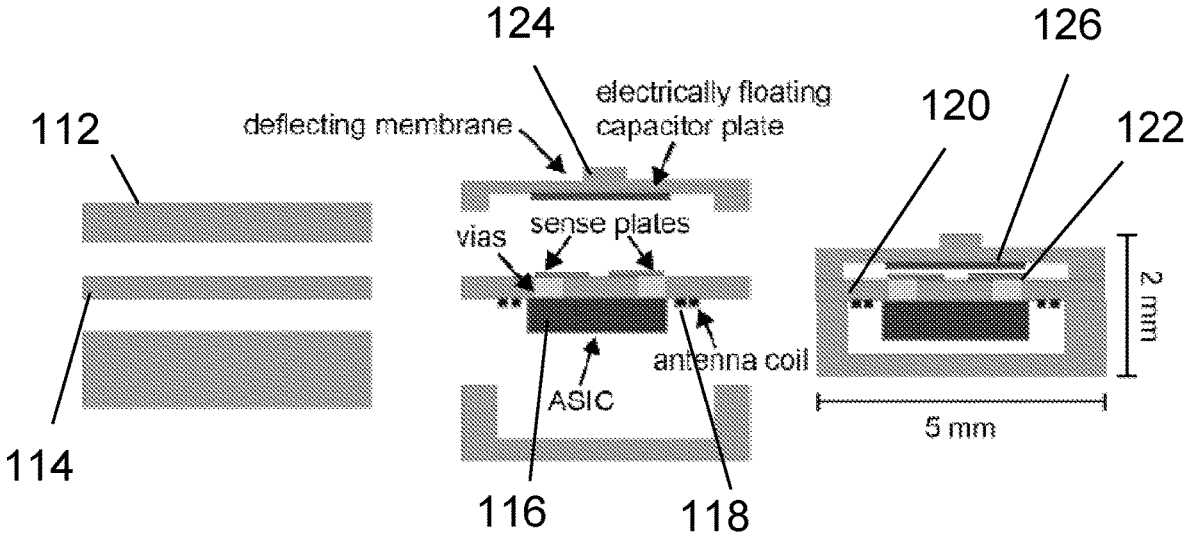
FIG. 18 are schematic diagrams of an implantable capacitive sensor according to an embodiment.

According to an embodiment, sensor fabrication is based on fused silica MEMS as shown in FIG. 18. A lower substrate 120 of fused silica has a lower inductor 122 electrodeposited on it using a plate-through photoresist mold approach. An upper substrate 124 of fused silica has a recess etched into it using isotropic wet etching and an upper inductor 126 is electrodeposited into the recess using the same plate-through-mold approach. The two substrates, 124 and 126, are hermetically sealed with laser-bonded and coated with a thin layer of silicone. An interesting property of fused silica is its extremely low thermal conductivity;

appropriate adjustment of laser parameters allows placement of temperature-sensitive components within very close proximity to the molten edge without component damage. The use of fused silica also offers low loss RF transparency, enabling both power and data to be supplied to and provided from the sensor with relative ease compared to other hermetic packaging technologies such as metals.

The multilevel silica-based hermetic encapsulation technology provides both normal and directionally-resolved shear strain sensing capability. The capacitive sensor 110 may be comprised of three fused silica wafers or substrates 114 as shown in the left side of FIG. 18. The upper and lower wafers have recesses (see the center of FIG. 18) and protrusions etched into them using photolithography and HF etching. Multiple upper capacitor electrodes are patterned into the recess of the upper plate 124; these electrodes, which are geometrically distributed for sensing the direction as well as the magnitude of applied forces, act as encapsulated, movable, electrically floating plates of the capacitive strain/shear sensor 110. On the center wafer 120, vias are formed which act as landing pads for multiple lower capacitor plates (which can resolve the position of the upper capacitor plates) as well as an RF transmission coil 118 for energy capture and data transmission, and an ASIC 116 that both cut at the edges to form the hermetically sealed device (see the right side of FIG. 18).

The capacitive sensor 110 is engineered to be sensitive to both normally-directed stress as well as laterally-directed stress (i.e., shear). Normally-directed stress will result in a common-mode increase in capacitor plates as the upper deflecting membrane moves uniformly downward due to the applied stress (i.e., see the middle diagram of FIG. 20F). Laterally-directed stress will result in a differential-mode change in capacitance, in which one capacitor will increase and the other will decrease depending on the direction of the applied shear (i.e., see the lower diagram of FIG. 20F). Multidimensional resolution can be achieved by multiple such capacitor plates formed within the package. The signal processing chip detects these capacitor changes and transduces them to an electrical signal that can be transmitted to a remote collection point.

Figures 19A, 19B, 19C:
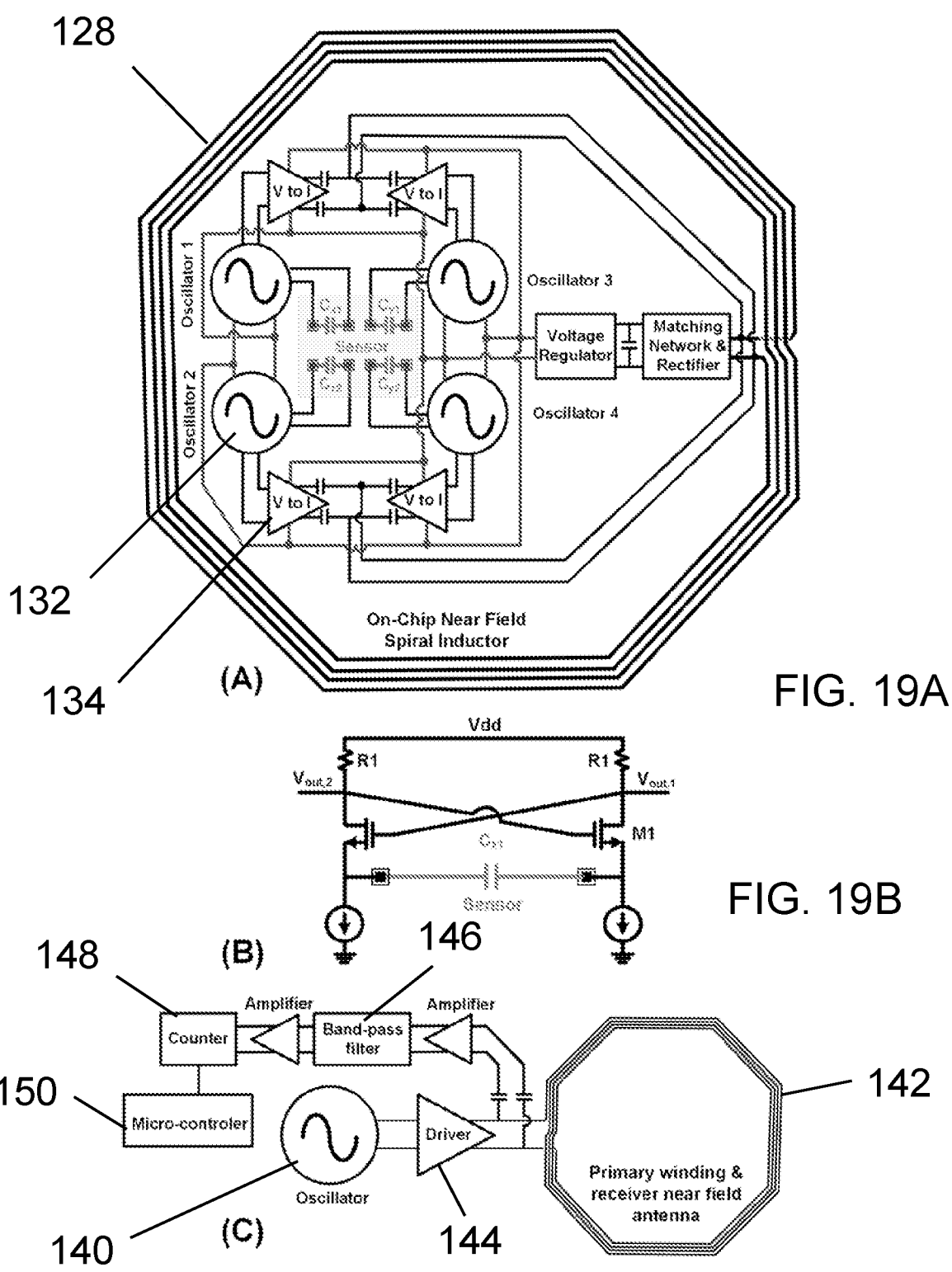
FIG. 19A is a schematic diagram of an implantable CMOS chip sensor according to an embodiment.
FIG. 19B is a schematic view of a relaxation oscillator of the sensor read-out unit according to an embodiment.
FIG. 19C is a schematic view of the wrist/base unit according to an embodiment.

FIG. 19A provides an example of an embodiment of an implantable sensor 102 which includes four capacitors and four oscillators. The implanted biomedical devices 102 use wireless powering and communication so as not to incur the infection risk of percutaneous leads, nor their psychological repercussions. Thus, the ASIC 116 for each of the capacitive sensors 110 of the implantable sensor 102 accomplishes the above referenced functions along with a base unit 104 worn at the wrist to which the data is transferred and from which power for the ASIC 116 is derived. The battery-less CMOS chip of the sensor 102 can be powered remotely using magnetic coupling, read-out the force sensor, and communicate force data to the base unit 104 on the wrist.

According to an embodiment, an on-chip spiral inductor 128 is used as both the secondary winding for inductive powering of the CMOS chip and as a near field transmit antenna. The induced signal in the on-chip inductor 128 is rectified by a full-wave rectifier implemented using zero-threshold mixed-oxide-semiconductor field-effect transistor (MOSFET) devices. See FIG. 19A. The rectified signal is used to power a relaxation oscillator 132 and a voltage-to-current driver (V-to-I) 134. A matching network (to create a resonance at the desired frequency) followed by a low threshold rectifying bridge and a voltage regulator are used to generate a 1.2 V supply voltage from the induced current. The generated 1.2 V is used to power up four relaxation oscillators 132. The frequencies of the four oscillators (1, 2, 3, 4) are set by the value of the sensor capacitors (Cx1, Cx2, Cy1, Cy2), respectively. Over the entire dynamic range of the force sensor, the frequency of these four oscillators remains within respective band with no overlap. Furthermore, the oscillation frequencies of two of the oscillators remain on the left side of the frequency of the powering signal while the frequencies of the other two oscillators remain on the right side of the frequency of the powering signal and, therefore, all four frequencies can easily be distinguished using an external receiver.

Figures 20A, 20B, 20C, 20D, 20E, 20F:
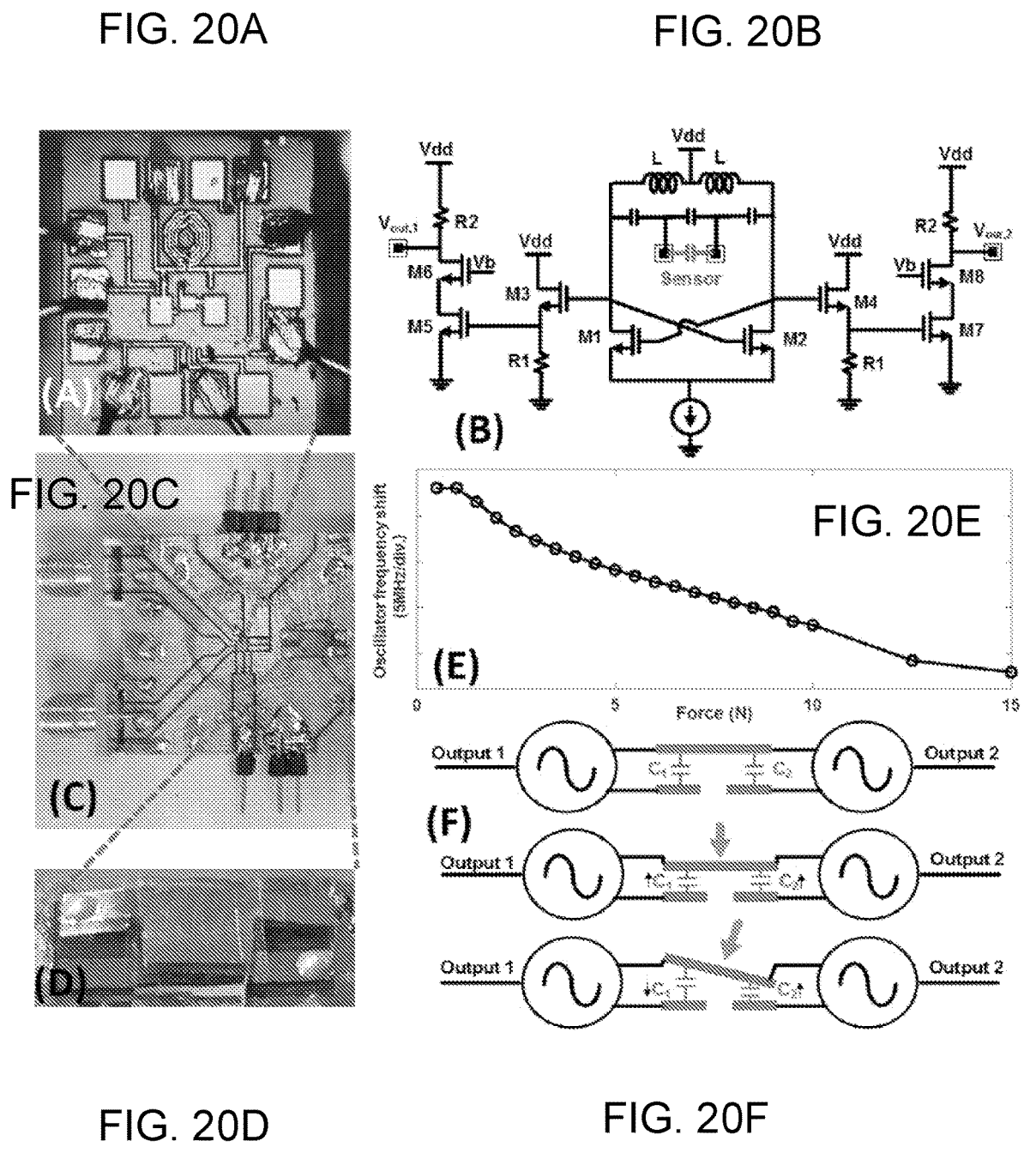

Under common mode operation, when a normal force is applied to the sensor, all four capacitors (Cx1, Cx2, Cy1, Cy2) will change together resulting in the frequency shift in all oscillators (1, 2, 3 and 4) to occur in the same direction (similar to the showing with two capacitors in the middle diagram of FIG. 20F). Under the differential mode operation, when a shear force along the x-axis is applied to the sensor, Cx1 and Cx2 will change in opposite directions resulting in opposite frequency shifts in oscillators 1 and 2. Similarly, when a shear force along the y-axis is applied to the sensor, Cy1 and Cy2 will change in opposite directions resulting in opposite frequency shifts in oscillators 3 and 4 (similar to the showing with two capacitors in the middle diagram of FIG. 20F). The receiver on the base unit 104 measures the output of all oscillators and can determine the amount and type (normal or shear) of the applied force. The output of four oscillators is converted to a current using voltage to current converters and is used to drive the on-chip spiral inductor 128.

FIG. 19A provides a schematic of the proposed CMOS chip sensor 102 where both normal and shear forces can be sensed and reported back to the base unit. FIG. 19B is a schematic of the relaxation oscillator as the custom sensor read-out unit. FIG. 19C provides a schematic view of the base unit 104.

FIG. 20A is a microphotograph of an embodiment of a CMOS chip 102 that contains a cross-coupled oscillator designed to interface with the fabricated MEMS-based capacitive force sensor where the oscillation frequency shift corresponding to the applied force is measured. FIG. 20B is a schematic of the CMOS sensor read-out chip 102. An example of a PCB for the CMOS chip and force sensor is shown in FIG. 20C, and an example of a capacitive force sensor is shown in FIG. 20D. FIG. 20E is a diagram of the measured frequency shift of the on-chip oscillator vs. applied normal force on the capacitive force sensor. To measure shear forces, two CMOS on-chip oscillators were connected to the force sensor as shown in FIG. 20F. FIG. 20G is a schematic of an embodiment having an integrated dual oscillator. FIG. 20H is a plot of frequency shift of the two integrated oscillators when a shear force was applied to the sensor. The plot shows that the frequency shift in the two oscillators occurred in opposite directions for applied shear force.

The sensor and associated CMOS chip can be powered by a variety of methods, including piezoelectric, near-field, or far-field methods. Ultrasonic powering can provide a relatively high power density of approximately $0.1 \text{ mW/cm}^2$ at up to 10-15 mm. However, the impedance mismatch at the distinct boundaries between air, tissue, and implant reduces the transfer efficiency. To solve this problem, magnetic resonance instead of electric or ultrasonic fields is used according to an embodiment. This is possible because at frequencies of approximately 10-MHz, the body itself acts as a communication channel with magnetic coupling.

Advantages of magnetic human body communication (MHBC) over galvanic or capacitive body communication are its insensitivity to noise from the environment or from changes in body posture. Using this MHBC strategy, an oscillator 140 generates the powering signal which is transferred to the primary winding 142 using a driver 144. See FIG. 19C. The same inductor 142 also acts as the receiver near-field antenna and is used to detect the sensor data transmitted by the implanted CMOS chip 102. To ease the data communication, the on-chip oscillator is designed such that its frequency over the dynamic range of the sensor 102 does not overlap with the powering signal and can be separated using filters 146 on the base unit 104.

The base unit 104 has four receive paths. Each path is design to monitor the frequency range associated with one of the oscillators as shown in FIG. 19A (using proper filtering followed by a counter 148). The outputs of the counters 148 are connected to a micro-controller 150 for detection and processing. The base unit 104 may be implemented on a PCB.

Figure 22:
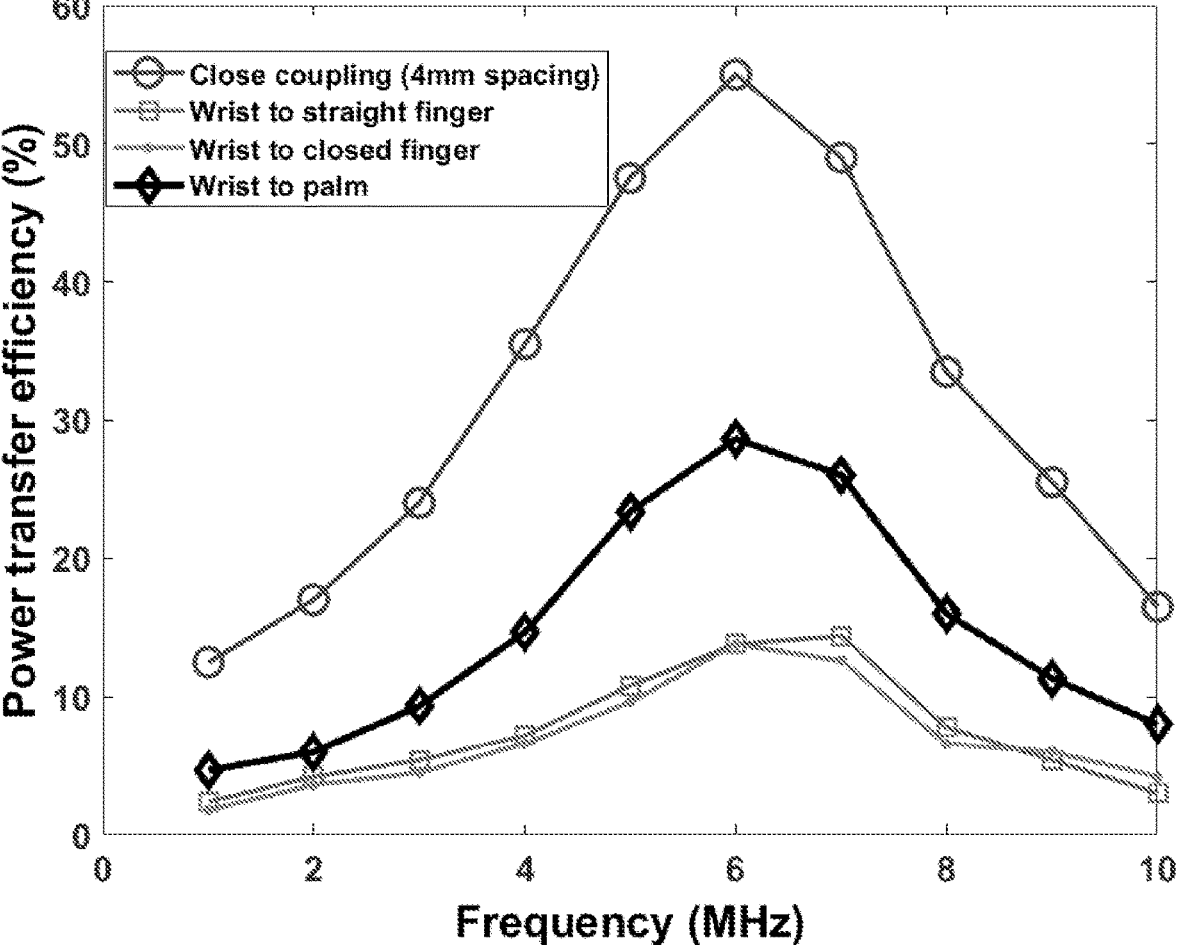
FIG. 22 is a diagram of experimental results of power transfer efficiency for the setup shown in FIG. 21.

As shown in FIG. 21, the primary coil 142 was worn as a wristwatch while the secondary coil was placed either on the fingertip (case A in FIG. 21) or on the palm (case B in FIG. 21). To measure the power transfer efficiency, the secondary coil was terminated to a 1-kW resistor and a 2-V peak-to-peak voltage was applied across the primary coil 142. Then, the raw, unfiltered power transfer efficiency versus frequency was measured. As a control, this was compared to the case where the primary and secondary coils were placed at 4-mm distance with the same load and drive (see FIG. 22). A power-frequency response curve is immediately evident from FIG. 22. Also, importantly, the response was agnostic to changes in finger position. Furthermore, the power transfer efficiency when secondary was placed on the palm was higher than the case that the secondary was placed on the fingertip. These measurements confirm the feasibility of the MHBC in the body region of interest.

The amplitude of the response was lower than when the coils were very close together (e.g., 8-mm). To compensate for this, a low noise amplifier (LNA) is placed after the receive coil in the wrist unit 104. Therefore, the wrist unit 104 has an additional LNA at the front-end and a wireless unit in the backend. The wireless unit can be specifically designed to communicate with other units such as brain implants 106. The external wrist unit 104 can be powered by a battery. However, since the MHBC has 5× lower signal, a passive voltage multiplier may be added after the rectifier (implemented using zero threshold MOSFET devices) to ensure ample supply voltage required for CMOS chip operation.

It is widely recognized that restoring somatosensation is critical to the success of limb reanimation. Embodiments disclosed herein offer significant advantages over current state of the art and immediately addresses a gap in the existing medical device market. A variety of sensors, ranging from simple strain gauges and accelerometers have been designed for integration into prosthetic hands. Developing an appropriate sensor system for the reanimated paralyzed hand is a unique challenge and patient population (paralyzed individuals verses amputees) and requires an innovative approach.

Sensorized gloves might be considered as a possible approach. In theory, many of the sensors used in prosthetics hands could work for a deafferented human hand if they were integrated into a sensorized glove. However, this strategy has major functional and aesthetic limitations. Gloves confound hand movements by introducing slip between the fingers and the manipulated object. Further, synthetic gloves are susceptible to damage from moisture and abrasion unlike native skin that evolved over millions of years to be perfectly adapted to manipulate objects throughout the life-span of the organism. Gloves also must be donned and doffed by an able-bodied assistant. Finally, wearing a bulky glove would likely decrease the psychological benefits conferred by restoring grasp in the native hand.

Another approach might be to use the native mechanical sensors of the skin. The skin of the fingertip is endowed with a dense array of mechanoreceptors that sense force and vibration and communicate this information along peripheral nerves back to the brain. These signals are precisely what is hoped to communicate to an individual with a reanimated hand. One could record from these peripheral nerves to extract sensory information as they would not be damaged acutely by SCI or stroke. However, there is considerable evidence that central nervous system injuries do, in the long term, cause dysfunction and degeneration of peripheral nerves and the mechanoreceptor end organs. Furthermore, this strategy would require a peripheral neural interface, which presents problems related to selectivity, stability, and longevity. No system to date has demonstrated this capacity.

Another approach is FES magnitude feedback which requires no additional sensors to deliver sensory cortical stimulation in proportion to the amount of applied FES, which is derived from decoded motor cortical activity and is correlated with grasping force. In effect, this would be an artificial implementation of reafference, providing the user with sensory consequences of the grasping action. This information could certainly be useful. However, this strategy would fail to provide exafference, or feedback about sensory signals generated by the environment. In grasping, exafferent signals are, for example, the shear forces on the skin generated by the weight of the grasped object or slip of that object. These externally-generated signals robustly drive peripheral and somatosensory cortical activity. This is clearly critical feedback even for basic grasping behaviors.

The implantable force sensors 102 described above solve many of the limitations of the aforementioned strategies. It would not interfere mechanically with grasping and would be entirely transparent to the user. It has the advantage over interfacing with native sensors of having a longer, if not unlimited, operational lifetime. Finally, the artificial sensor 102 can be designed to sense the force vector (normal and shear forces) acting on the skin to provide the user with both reafference and exafference.

As with all biomedical implants, however, there are a number of technical challenges including size, biocompatibility, and data telemetry. These challenges are addressed with a number of innovations. First, advanced MEMS and integrated circuit designs are used to produce a minimum-volume device 102 that can be inserted into the fatty tissue below the skin (i.e., hypodermis) of selected hand locations. Second, a multilevel silica-based hermetic encapsulation for the device ensures biocompatibility and device integrity in vivo while further minimizing the overall size. Third, a telemetry strategy using magnetic human body communication (MHBC) is utilized such that the implanted device can be powered by and communicate with a wireless receiver 104 worn at the wrist.

Accordingly, an individual with paralysis due to spinal cord injury or stroke, where both sensory and motor functions are disrupted, the tactile feedback system can be used in concert with a system to restore movement. Battelle, along with several academic institutions, has demonstrated in paralyzed humans a system in which recorded brain signals drive electrical stimulation of paralyzed muscles to restore hand grasping abilities. However, none of the known systems have yet provided any tactile feedback to the user. So, the skin remains numb and the restored movements, without tactile feedback, are clumsy and awkward. In contrast, the implantable sensory-restoration system 100 according to embodiments disclosed herein could be easily integrated with these motor-restoration systems to meet this need. Importantly, since the wireless communication of the embodiments disclosed herein occurs in the MHz range, it will not be corrupted by the kHz range electrical stimulation patterns used to reanimate paralyzed muscles.

While the invention has been described with reference to particular embodiments, it will be appreciated that modifications can be made without departing from the spirit of the invention. Such modifications are intended to fall within the scope of the appended claims.

What is claimed is:

1. A sensory system (100) for use in restoring sensation to a hand of a patient, comprising:

at least one force sensor (102) for being implanted subcutaneously within a hand of a patient; and a separate base unit (104) for powering said at least one sensor (102) and for receiving data from said at least one sensor (102);

wherein said at least one force sensor (102) is configured to transmit wireless communication signals to said base unit (104) in response to forces sensed by said at least one sensor (102), is configured to transmit the wireless communication signals to said base unit (104) by magnetic human body communication (mHBC), and is configured to sense normal and shear components of forces and to transmit data concerning the forces to said base unit (104);

wherein said at least one force sensor (102) is for being implanted within a finger or palm of a hand of the patient and said base unit (104) is for being worn externally around a wrist of the patient; and wherein the at least one sensor (102) includes at least four separate sensor capacitors (Cx1, Cx2, Cy1, Cy2) and four oscillators (1, 2, 3, 4), wherein an oscillation frequency band of each of the four oscillators (1, 2, 3, 4) does not overlap with the other of the four oscillators (1, 2, 3, 4), and wherein the oscillation frequencies of two of the four oscillators (1, 2, 3, 4) are on one side of a frequency of a powering signal generated by the base unit (104), and the oscillation frequencies of the other two of the four oscillators (1, 2, 3, 4) are on an opposite side of the frequency of the powering signal.

2. The sensory system (100) according to claim 1, wherein said at least one force sensor (102) is a battery-less capacitive pressure sensor (110), wherein the data provides information with respect to changes in capacitance sensed by the at least one force sensor (102), and wherein said battery-less capacitive pressure sensor (110) is microfabricated within a biocompatible, hermetically sealed fused silica package (24), containing an application-specific integrated circuit (116).

3. The sensory system (100) according to claim 2, wherein said at least one sensor (102) includes a coil (118, 128) via which the wireless signals are transmitted to said base unit (104) and via which signals are received to power said at least one sensor (102).

4. The sensory system (100) according to claim 1, wherein the base unit (104) is configured to transmit data concerning forces sensed by said at least one sensor (102) to neural implants (106) for use in driving muscle stimulators (108).

5. The sensory system (100) according to claim 1, wherein the four separate sensor capacitors (Cx1, Cx2, Cy1, Cy2) are aligned such that when a normal force is applied to each of the four separate sensor capacitors (Cx1, Cx2, Cy1, Cy2), a frequency shift will occur for each of the four oscillators (1, 2, 3, 4) in a same direction, and when a shear force is applied in a particular direction, a frequency shift will occur in an opposite direction for at least one of the sensor capacitors (Cx1, Cx2, Cy1, Cy2).

6. The sensory system (100) according to claim 1, wherein the base unit (104) includes an oscillator (140) for generating a power signal for the at least one sensor (102) and a driver (144) for transferring the power signal to an inductor (142) which transmits the power signal.

7. The sensory system (100) according to claim 6, wherein the inductor (142) is an antenna for receiving the communication signals transmitted by the at least one sensor (102), and wherein the base unit (104) further includes a filter (146), counter (148), and micro-controller (150) for detection and processing of the communication signals.

8. A sensory system (10) for use in restoring sensation to a foot of a patient, comprising:

at least one force sensor (12) for being implanted subcutaneously within a foot of a patient; and a separate base unit (18) for powering said at least one sensor (12) and for receiving data from said at least one sensor (12);

wherein said at least one force sensor (12) is configured to transmit wireless communication signals to said base unit (18) in response to forces sensed by said at least one sensor (12), is configured to transmit the wireless communication signals to said base unit (18) by magnetic human body communication (mHBC), and is configured to sense normal and shear components of forces and to transmit data concerning the forces to said base unit (18); and wherein said at least one force sensor (12) is for being implanted subcutaneously on a plantar surface of a foot of a patient, wherein said base unit (18) is for being implanted subcutaneously in a leg of the patient and has a nerve cuff (20) for applying peripheral nerve stimulation to a tibial nerve of the patient, and wherein said base unit (18) is configured to apply peripheral nerve stimulation to the tibial nerve based on the wireless communication signals received from said at least one force sensor (12);

wherein said at least one force sensor (12) and said base unit (18) are configured to provide a closed-loop system transmitting tactile sensations from the plantar surface of the foot via said at least one force sensor (12) to the tibial nerve via the peripheral nerve stimulation applied by said base unit (18);

wherein said at least one force sensor (12) is configured to sense normal and shear components of ground reaction forces experienced during standing and walking and to transmit data concerning the forces to said base unit (18);

wherein said base unit (18) includes an application-specific integrated circuit (46) for communicating with said at least one sensor (12); and wherein said application-specific integrated circuit (46) of said base unit (18) is configured to transmit a carrier signal via a base unit coil (54) to said at least one sensor (12) and receive said communication signals from said at least one sensor (12) as backscattered signals corresponding to a measured force vector from said at least one sensor (12).

9. The sensory system (10) according to claim 8, wherein said base unit (18) is configured for being implanted subcutaneously adjacent a knee of the patient.

10. The sensory system (10) according to claim 8, wherein said base unit (18) includes a microcontroller (44) for determining characteristics of the peripheral nerve stimulation to be applied to the tibial nerve based on the communication signals received from said at least one sensor (12).

11. The sensory system (10) according to claim 8, wherein said at least one sensor (12) includes a plurality of separate sensors (22*a*, 22*b*, 22*c*) each for being separately implanted subcutaneously within the foot, and wherein said application-specific integrated circuit (46) of said base unit (18) communicates with each of said sensors (22*a*, 22*b*, 22*c*) through different frequency channels.

12. The sensory system (10) according to claim 8, wherein said application-specific integrated circuit (46) of said base unit (18) is configured to drive said nerve cuff (20) to stimulate the tibial nerve.

13. The sensory system (10) according to claim 8, wherein said base unit (18) is battery powered and includes at least one battery (62), and wherein said base unit (18) includes an accelerometer (48).

14. The sensory system (10) according to claim 9, further comprising an external unit (58) that communicates with said base unit (18) via wireless communication signals and that controls operation of said base unit (18) and monitors information passed between said at least one sensor (12) and said base unit (18).

\* \* \* \* \*